United States Patent [19]
Los

[11] Patent Number: 4,921,961
[45] Date of Patent: May 1, 1990

[54] 2-CARBAMOYL-3-QUINOLINECARBOXYLIC ACIDS AND SALTS AS INTERMEDIATES FOR THE PREPARATION OF HERBICIDAL 2-(5-ISOPROYL-5-METHYL-4-OXO-2-IMIDAZOLIN-2-YL)-3-QUINOLINECARBOXYLIC ACIDS

[75] Inventor: Marinus Los, Pennington, N.J.

[73] Assignee: American Cyanamid Company, Stamford, Conn.

[21] Appl. No.: 222,449

[22] Filed: Jul. 18, 1988

Related U.S. Application Data

[60] Division of Ser. No. 860,205, May 6, 1986, Pat. No. 4,769,462, which is a continuation-in-part of Ser. No. 382,041, May 25, 1982, Pat. No. 4,638,068, which is a continuation-in-part of Ser. No. 252,704, Apr. 9, 1981, abandoned, which is a continuation-in-part of Ser. No. 155,909, Jun. 2, 1980, abandoned, and a continuation-in-part of Ser. No. 155,910, Jun. 2, 1980, abandoned, and a continuation-in-part of Ser. No. 155,867, Jun. 2, 1980, abandoned, and a continuation-in-part of Ser. No. 155,908, Jun. 2, 1980, abandoned, and a continuation-in-part of Ser. No. 155,865, Jun. 2, 1980, abandoned.

[51] Int. Cl.$^5$ ............................................. C07D 215/14
[52] U.S. Cl. .................................... 546/169; 546/170
[58] Field of Search ...................... 71/92; 546/169, 170

[56] References Cited

U.S. PATENT DOCUMENTS 2,304,830 12/1942 Katzman ............................. 546/169
2,798,070 7/1957 Cain .................................... 546/169
4,518,780 5/1985 Barton et al. ....................... 548/322
4,638,068 1/1987 Los ..................................... 546/169

FOREIGN PATENT DOCUMENTS 0041623 12/1981 European Pat. Off. .

Primary Examiner—Anton H. Sutto
Assistant Examiner—Andrew G. Rozycki
Attorney, Agent, or Firm—John W. Hogan, Jr.

[57] ABSTRACT

The invention is novel 2-carbamoylnicotinic and 3-quinolinecarboxylic acids and esters which are intermediate compounds for the preparation of 2-(2-imidazolin-2-yl)pyridine and quinoline herbicides.

4 Claims, No Drawings

2-CARBAMOYL-3-QUINOLINECARBOXYLIC ACIDS AND SALTS AS INTERMEDIATES FOR THE PREPARATION OF HERBICIDAL 2-(5-ISOPROYL-5-METHYL-4-OXO-2-IMIDAZOLIN-2-YL)-3-QUINOLINECARBOXYLIC ACIDS

This is a divisional of copending U.S. application Ser. No. 860,205, filed May 6, 1986, now U.S. Pat. No. 4,769,462 which is a continuation-in-part of U.S. application Ser. No. 382,041, filed May 25, 1982, now U.S. Pat. No. 4,638,068, which is in turn a continuation-in-part of U.S. application Ser. No. 252,704, filed Apr. 9, 1981, now abandoned, which is a continuation-in-part of U.S. Ser. Nos. 155,909; 155,910; 155,867; 155,908; and 155,865 which were all filed June 2, 1980 and are all now abandoned.

SUMMARY OF THE INVENTION

This invention relates to the novel intermediates:
A. 2-[(1-carbamoyl-1,2-dimethylpropyl)carbamoyl]-5-ethylnicotinic acid;
B. 2-(1-carbamoyl-1,2-dimethylpropyl)carbamoyl]-5-methylnicotinic acid;
C. methyl 2-[(1-carbamoyl-1,2-dimethylpropyl)carbamoyl]-6-phenylnicotinate;
D. (R)-(−) 2-[(1-carbamoyl-1,2-dimethylpropyl)carbamoyl]-3-quinolinecarboxylic acid;
E. 2-amino-2,3-dimethylbutyramide 2-[(1-carbamoyl-1,2-dimethylpropyl)carbamoyl]-6-(difluoro-methoxy)-3-quinoline carboxylate;
F. methyl 2-[(1-carbamoyl-1,2-dimethylpropyl)carbamoyl]-6-p-tolylnicotinate;
G. methyl 2-[(1-carbamoyl-1-methylethyl)carbamoyl]-nicotinate;
H. triethylammonium 2-[(1-carbamoyl-1,2-dimethylpropyl)carbamoyl]nicotinate;
I. 2-[(1-carbamoyl-1,2-dimethylpropyl)carbamoyl]-5-chloro-6-fluoro-3-quinolinecarboxylic acid;
J. 2-[(1-carbamoyl-1,2-dimethylpropyl)carbamoyl]-7-fluoro-3-quinolinecarboxylic acid;
K. 2-[(1-carbamoyl-1,2-dimethylpropyl)carbamoyl]-8-chloro-5-methoxy-3-quinolinecarboxylic acid;
L. 2-[(1-carbamoyl-1-methylpropyl)carbamoyl]nicotinic acid;
M. furfuryl 2-[(1-carbamoyl-1,2-dimethylpropyl)carbamoyl]nicotinate;
N. 6-butoxy-2-[(1-carbamoyl-1,2-dimethylpropyl)carbamoyl]nicotinic acid;
which are useful in the synthesis of herbicidal 2-(2-imidazolin-2-yl)pyridine and quinoline compounds disclosed in European Patent 41623 (1985) which is incorporated herein by reference.

These intermediate 2-carbamoylnicotinic and 3-quinolinecarboxylic acids may be prepared by the reaction of an appropriately substituted formula (I) quinolinic anhydride with an aminocarboxamide or aminothiocarboxamide depicted by formula (II) to yield an isomeric mixture of the formula (IIIa) intermediates carbamoylnicotinic or a 3-quinolinecarboxylic acid and formula (IIIb) carbamoylpicolinic or quinaldic acid. This reaction is carried out, preferably using equivalent amounts of the anhydride and carboxamide or thiocarboxamide, in the presence of an inert organic solvent such as a low-boiling ether (diethyl ether, tetrahydrofuran, dimethoxyethane), acetonitrile, ethyl acetate or a halogenated hydrocarbon at a temperature between about 20° and 60° C. and preferably 25° to 30° C., under a blanket of inert gas such as nitrogen. When the reaction is essentially complete, the intermediate product is isolated by any convenient means, e.g., filtration, distillation of the solvent or by extraction into aqueous base if the solvent is water-immiscible giving the isomeric pyridine or quinoline acid products shown as formula (IIIa) and formula (IIIb) in Flow Diagram I.

To prepare the herbicidal product of formula IV the intermediate mixture is heated to a temperature of from 25° to about 110° C. (i.e., reflux temperature) with about 2 to 10 molar equivalents of aqueous or aqueous alcoholic sodium or potassium hydroxide, preferably under a blanket of inert gas such as nitrogen. The mixture is cooled to about 25° C. and acidified to pH 2 to 4 with a strong mineral acid such as hydrochloric acid or sulfuric acid to give the 2-(2-imidazolin-2-yl) pyridine or quinoline (IV). If the product is insoluble in water, it will precipitate from the aqueous phase and can be recovered by filtration or extraction. If the product is soluble in water, the mixture can be extracted with an organic solvent such as ether or methylene chloride, and the extract concentrated to provide the herbicidally effective 2-(5,5-disubstituted-4-oxo-(or thiono)-2-imidazolin-2-yl)nicotinic or 3-quinolinecarboxylic acids, encompassed by formula (IV).

This process is described in the U.S. Letters Patent of Jerry Michael Barton, Don Wesley Long and Kenneth Dale Lotts, 4,518,780, issued May 21, 1985 and is illustrated below in Flow Diagram I.

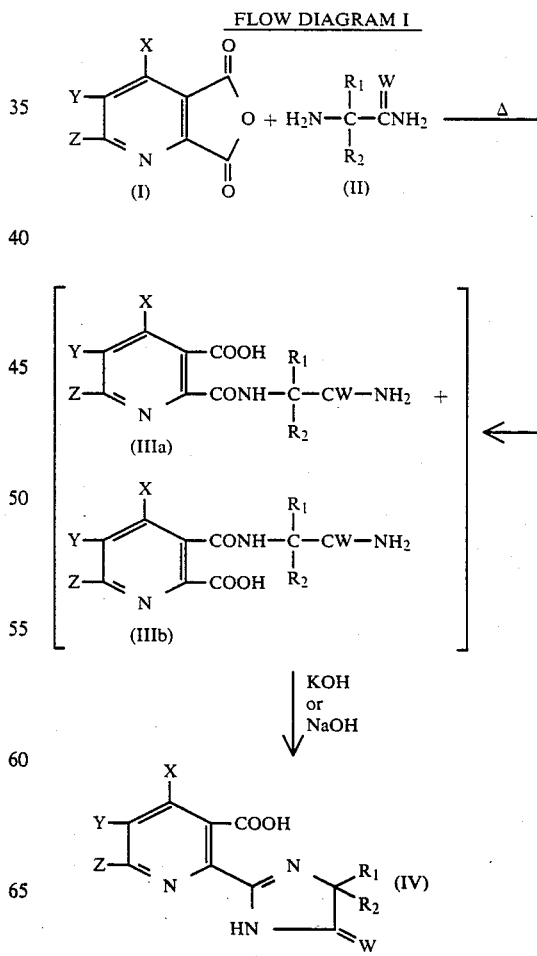

wherein $R_1$ is $C_1$–$C_4$ alkyl; $R_2$ is $C_1$–$C_4$ alkyl or $C_3$–$C_6$ cycloalkyl; and when $R_1$ and $R_2$ are taken together, along with the carbon to which they are attached, they may represent $C_3$–$C_6$ cycloalkyl optionally substituted with methyl, and when $R_1$ and $R_2$ are not the same, the optical isomers thereof; W is O or S; X is hydrogen, or $C_1$–$C_4$ alkyl, Y is hydrogen, halogen, $C_1$–$C_4$ alkyl, $C_1$–$C_4$ alkoxy, trifluoromethyl, trichloromethyl, difluoromethoxy, diloweralkylamino, $C_1$–$C_4$ alkylthio, phenyl, phenoxy, or phenyl or phenoxy substituted with one $C_1$–$C_4$ alkyl, $C_1$–$C_4$ alkoxy or halogen; Z represents hydrogen, $C_1$–$C_4$ alkyl, trifluoromethyl, trichloromethyl, phenyl or phenyl substituted with one $C_1$–$C_4$ alkyl, $C_1$–$C_4$ alkoxy or halogen; and, when taken together, Y and Z may form a ring in which YZ are represented by the structure: —$(CH_2)_n$—, where n is an integer selected from 3 to 5, provided that X is hydrogen; or YZ is

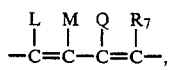

where L, M, Q and $R_7$ each represent hydrogen, halogen, $C_1$–$C_4$ alkyl, $C_1$–$C_4$ alkoxy, $C_1$–$C_4$ haloalkyl, difluoromethoxy, diloweralkylamino, $C_1$–$C_4$ alkylthio, nitro, phenyl, phenoxy, or mono-substituted phenyl or phenoxy where the substituent is one $C_1$–$C_4$ alkyl, $C_1$–$C_4$ alkoxy or halogen; with the proviso that only one of L, M. Q or $R_7$ may represent a substituent other than hydrogen, halogen, $C_1$–$C_4$ alkyl or $C_1$–$C_4$ alkoxy.

Salts of formula IIIa compounds are readily prepared from these acids by procedures well known in the art, while esters of these acids represented by formula (VI) in Flow Diagram II below, may be prepared by the reaction of an appropriately substituted 5,7-dihydro-5,7-dioxo-6H-pyrrolo[3,4b]pyridine-6-acetamide represented by formula VII with an alkali metal alkoxide of formula VIII in the presence of the appropriate alcohol.

Formula VI esters may then be used for the preparation of the formula (V) 2-(2-imidazolin-2-yl)pyridine and quinolinic esters. Cyclization of a 2-carbamoyl nicotinic or 3-quinolinic acid ester, represented by formula (VI), with phosphorus pentachloride at an elevated temperature, generally between about 60° C. and 100° C., occurs. The reaction is preferably conducted in the presence of an inert organic solvent, such as toluene or benzene. Good yields of the hydrochloride salt of the desired formula (V) ester are attained. The hydrochloride salt is then readily converted to the formula (V) ester by dissolution of the acid addition salt in water and neutralization of the thus-prepared solution with base, such as sodium or potassium carbonate. The overall reactions can be illustrated as follows:

FLOW DIAGRAM II

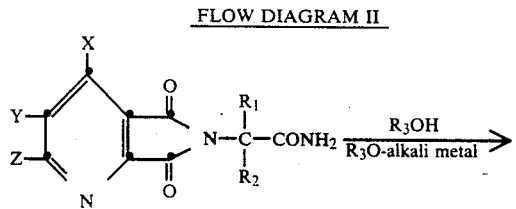

-continued
FLOW DIAGRAM II

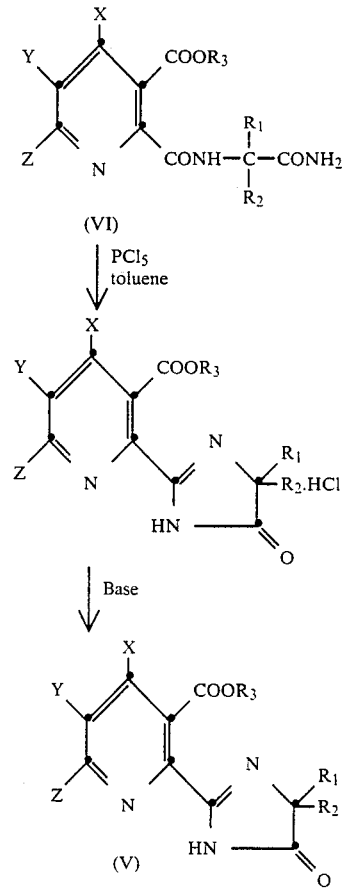

wherein $R_3$ is
$C_1$–$C_{12}$ alkyl optionally substituted with one of the following groups: $C_1$–$C_3$ alkoxy, halogen, hydroxy, $C_3$–$C_6$ cycloalkyl, benzyloxy, furyl, phenyl, halophenyl, loweralkylphenyl, loweralkoxyphenyl, nitrophenyl, carboxyl, loweralkoxycarbonyl, cyano or triloweralkylammonium;
$C_3$–$C_{12}$ alkenyl optionally substituted iwth one of the following groups: $C_1$–$C_3$ alkoxy, phenyl, halogen or loweralkoxycarbonyl or with two $C_1$–$C_3$ alkoxy groups or two halogen groups:
$C_3$–$C_6$ cycloalkyl optionally substituted with one or two $C_1$–$C_3$ alkyl groups; or
$C_3$–$C_{10}$ alkynyl optionally substituted with one or two $C_1$–$C_3$ alkyl groups and $R_1$, $R_2$, X, Y and Z are as hereinabove described.

In still another embodiment for the preparation of the formula (V) 2-(2-imidazolin-2-yl)pyridine or quinoline esters of the present invention, the cyclization of a carbamoyl nicotinic or 3-quinolinecarboxylic acid esters represented by formula (VI) is accomplished using a mixture of phosphorus pentachloride and phosphorus oxychloride. The reaction mixture is stirred at room temperature from about four to eight hours and then the $POCl_3$ removed in vacuo. The remaining residue is dispersed in an organic solvent such as toluene. The solvent is removed and the residue dispersed in water and heated to between 80° C. and 100° C. After cooling, the pH of the aqueous mixture is adjusted to 5–6 with sodium bicarbonate, and the product extracted into methylene chloride to give the desired formula (V)

2-(2-imidazolin-2-yl)pyridine or quinoline ester. The reaction can be graphically illustrated as follows:

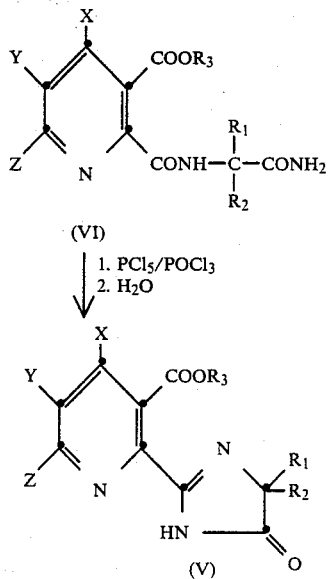

where R$_3$ is a substituent other than hydrogen or a salt-forming cation as described above, and R$_1$, R$_2$, X, Y and Z are as described above.

EXAMPLE 1

Preparation of 5,7-Dihydro-alpha-isopropyl-alphamethyl-5,7-dioxo-6H-pyrrolo[3,4-b]pyridine-6-acetamide To 330 mL concentrated sulfuric acid is added portion wise with thorough stirring 298 g of finely divided 5,7-dihydro-alpha-isopropyl-alpha-methyl-5,7-dioxo-6H-pyrrolo[3,4-b]pyridine-6-acetonitrile so that the temperature did not go about 72° C. After the addition the temperature is adjusted to 60°–65° C. and maintained there for 1½ hours. The mixture is cooled, quenched with ice and finally diluted to approximately 4 liters. After adding 454 g sodium acetate and cooling at 0° C. for 2 hours the mixture is filtered, the solids collected and washed twice with 500 mL water containing sodium acetate followed by water to remove all the sulfuric acid. The solid is dried to give 289 g of product, mp 176°–178° C. Material made in a similar way and analytically pure had mp 188°–190° C.

Employing the appropriate pyrrolopyridineacetonitrile in the above procedure, a variety of other pyrrolopyridineacetamides can be prepared including the following:

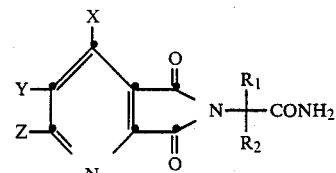

| R$_1$ | R$_2$ | X | Y | Z |
|---|---|---|---|---|
| CH$_3$ | CH(CH$_3$)$_2$ | H | H | tolyl |
| CH$_3$ | CH(CH$_3$)$_2$ | H | C$_2$H$_5$ | H |
| CH$_3$ | CH(CH$_3$)$_2$ | H | CH$_3$ | H |
| CH$_3$ | CH(CH$_3$)$_2$ | H | H | OC$_4$H$_9$ |

-continued

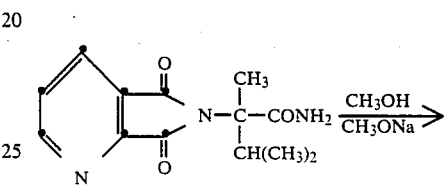

| R$_1$ | R$_2$ | X | Y | Z |
|---|---|---|---|---|
| CH$_3$ | CH(CH$_3$)$_2$ | H | H | phenyl |

EXAMPLE 2

Preparation of the intermediate Methyl 2-[(1-carbamoyl-1,2-dimethylpropyl)carbamoyl]nicotinate

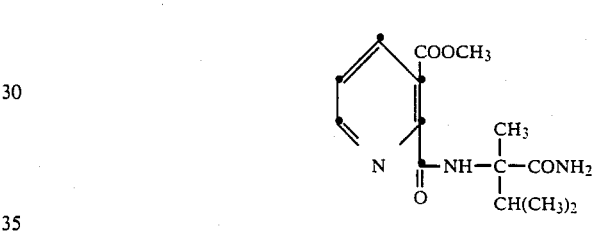

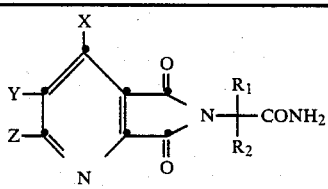

Sodium hydride (0.47 g of a 50% suspension in mineral oil) is reacted with 500 mL dry methanol under nitrogen. To this is added 51.4 g of 5,7-dihydroalpha-isopropyl-alpha-methyl-5,7-dioxo-6H-pyrrolo [3,4-b]pyridine-6-acetamide and the mixture stired at room temperature overnight. The mixture is concentrated, the residue dissolved in methylene chloride and the solution washed first with 150 mL water followed by 150 mL brine. After drying (Na$_2$SO$_4$), the organic phase is concentrated and the residue crystallized from ether to give 47.85 g of product which is analytically pure mp 108°–145° C. with decomposition.

Following the above procedure but substituting the appropriately substituted acetamide for 5,7-dihydro-alpha-isopropyl-alpha-methyl-5,7-dioxo-6H-pyrrolo[3,4-b]pyridine-6-acetamide and the appropriate alcohol and alkali metal alkoxide yields the following intermediate compounds:

(A) furfuryl 2-[(1-carbamoyl-1,2-dimethylpropyl carbamoyl]nicotinate, light yellow glass;
(B) methyl 2-[(1-carbamoyl-1,2-dimethylpropyl) carbamoyl]-6-phenylnicotinate, mp 166°–168° C.;
(C) methyl 2-[(1-carbamoyl-1-methylethyl) carbamoyl]nicotinate, mp 157.5°–158.5° C.;
(D) methyl 2-[(1-carbamoyl-1,2-dimethylpropyl) carbamoyl]-6-p-tolylnicotinate, mp 160°–161° C.;
(E) methyl 2-[(1-carbamoyl-1,2-dimethylpropyl)carbamoyl]-5-ethylnicotinate; and
(F) methyl 2-[(1-carbamoyl-1,2-dimethylpropyl)carbamoyl]-5-methylnicotinate.

EXAMPLE 3

Preparation of the herbicide 2-(5-isopropyl-5-methyl-4-oxo-2-imidazolin-2-yl)nicotinic acid

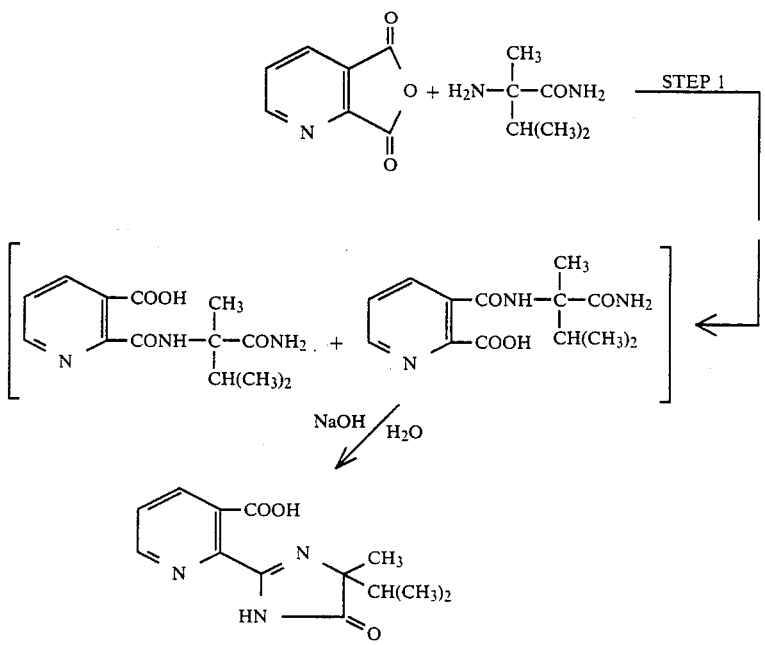

To a stirred suspension of 2,3-pyridinedicarboxylic anhydride (30 g) in 150 mL of acetonitrile is added a solution of 2-amino-2,3-dimethylbutyramide (28 g) in 140 mL of acetonitrile at 25°–30° C. The mixture is stirred for two hours. The solvent is removed at 50° C. and reduced pressure. The residual gum is dissolved in 230 mL of 2.6N sodium hydroxide and heated to 80° C. for one and one-half hours.

The mixture is cooled to 25° C. and acidified to a pH of 3 with 65 mL of 37% hydrochloric acid. The resulting solution is extracted with two 200 mL portions of methylene chloride. The extracts are concentrated to a residue of 33 g of the desired herbicide product, mp 160°–165° C.

After standing overnight, the aqueous layer deposits 3.8 g of the picolinic acid isomer, mp 155°–157° C. (dec.).

Other intermediates of the invention can be prepared by step 1 of the above procedure, using the appropriately substituted 2,3-pyridinedicarboxylic acids and/or the appropriate 2-amino-2,3-disubstituted amide or thioamide. These intermediates of the invention include:

(A) 2-[(1-carbamoyl-1,2-dimethylpropyl)carbamoyl]-5-ethylnicotinic acid, mp 121°–124° C.;
(B) 2-[(1-carbamoyl-1,2-dimethylpropyl)carbamoyl]-5-methylnicotinic acid, mp 172°–174° C.;
(C) 2-[(1-carbamoyl-1-methylpropyl)carbamoyl]nicotinic acid, mp 183°–185° C.; and
(D) 6-butoxy-2-[(1-carbamoyl-1,2-dimethylpropyl)carbamoyl]nicotinic acid.
(E) 2-[(1-carbamoylcyclohexyl)carbamoyl]nicotinic acid.

These acids are readily converted to salts by combining the appropriate acid and base in an 1:1 equivalent ratio in an inert solvent such as $CH_3OH$; $C_2H_5OH$; THF or the like, followed by removal of the solvent.

EXAMPLE 4

Preparation of 2,3-quinolinedicarboxylic anhydride

A mixture of 2,3-quinolinedicarboxylic acid-trihydrate (0.141 mol) in acetic anhydride (125 mL) is heated at 85° C. for ½ hour and then at 100° C. for 1 hour. The reaction mixture is then cooled to room temperature, filtered and the solids washed with ethyl ether to afford the desired 2,3-quinolinedicarboxylic anhydride, mp 225°–228° C.

Utilizing the above procedure but substituting the appropriately substituted 2,3-quinolinedicarboxylic acid for 2,3-quinolinedicarboxylic acid-trihydrate, yields the following substituted 2,3-quinolinedicarboxylic anhydrides.

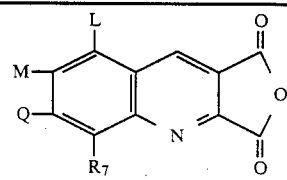

| L    | M    | O      | $R_7$ |
|------|------|--------|-------|
| Cl   | F    | H      | H     |
| H    | OCH₃ | H      | Cl    |
| H    | H    | F      | H     |
| OCH₃ | H    | F      | Cl    |
| H    | H    | OC₂H₅  | H     |

EXAMPLE 5

Preparation of intermediate 2-[(1-carbamoyl-1,2-dimethylpropyl)carbamoyl]-3-quinolinecarboxylic acid A solution of 2,3-quinolinedicarboxylic anhydride (0.37 mol) in tetrahydrofuran (THF, 250 mL) is stirred at 5° C. under a drying tube, and a solution of 2-amino-2,3-dimethylbutyramide (0.37 mol) in THF (50 mL) added thereto, in small increments, over a 15 minute period. The reaction mixture is allowed to warm slowly to room temperature for an extended period of time, i.e. about 17 hours. The solvent is evaporated in vacuo to afford a gummy residue, which is triturated with hot ethyl acetate (400 mL) and then filtered to afford the desired 2-[(1-carbamoyl-1,2-dimethylpropyl)carbamoyl]-3-quinolinecarboxylic acid, mp 172.5°–173.5° C.

Utilizing the above procedure but substituting the appropriately substituted 2,3-quinolinedicarboxylic anhydride for 2,3-quinolinedicarboxylic anhydride yields the following 2-[(1-carbamoyl-1,2-dimethylpropyl)carbamoyl]-1,2-dimethylpropyl)carbamoyl]-3-quinolinecarboxylic acids.

| L    | M    | O      | R7 | mp °C.              |
|------|------|--------|----|---------------------|
| Cl   | F    | H      | H  | 212–216             |
| H    | H    | H      | H  | 183–185 (R)-(−)isomer |
| H    | OCH3 | H      | Cl | 249–252             |
| H    | H    | OC2H5  | H  | 194.5–195.5         |
| H    | H    | F      | H  | 174–176             |
| OCH3 | H    | H      | Cl | 249–252             |

EXAMPLE 6

Preparation of herbicidal 2-(5-isopropyl-5-methyl-4-oxo-2-imidazolin-2-yl)-3-quinolinecarboxylic acid A solution of 2-[(1-carbamoyl-1,2-dimethylpropyl)carbamoyl]-3-quinolinecarboxylic acid (0.152 mol), in water (50 mL) containing sodium hydroxide (0.06 mol) is heated at 75° to 80° C. for 2 hours. The solution is cooled in an ice bath and acidified with concentrated hydrochloric acid, added in small increments. The resulting precipitate is filtered, washed with water, air dried, and recrystallized from acetone to afford the 2-(5-isopropyl-5-methyl-4-oxo-2-imidazolin-2-yl)-3-quinolinecarboxylic acid, mp 239°–243.5° C.

Utilizing the above procedure and substituting the appropriate intermediate 3-quinolinecarboxylic acid for 2-[(1-carbamoyl-1,2-dimethylpropyl)carbamoyl]-3-quinolinecarboxylic acid yields the compounds illustrated below; all of which are highly effective herbicidal agents.

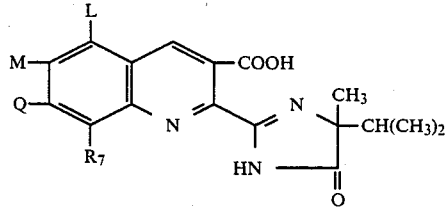

| L     | M       | O   | R7   | mp °C.      |
|-------|---------|-----|------|-------------|
| H     | NO2     | H   | H    | 241.5–242   |
| H     | OC6H5   | H   | H    | 223         |
| H     | H       | H   | OCH3 | 258.5–261   |
| H     | CF3     | H   | H    | 215–218     |
| H     | C6H5    | H   | H    | 209.5–212   |
| H     | CH3     | CH3 | H    | 238–240     |
| OCH3  | H       | H   | OCH3 | 249–250     |
| H     | C2H5    | H   | H    | 179.5–180.5 |
| H     | C4H9    | H   | H    | 149–150.5   |
| H     | H       | CH3 | CH3  | 238–240     |
| H     | OCHF2   | H   | H    | 206–209     |
| (+) H | Cl      | H   | H    |             |

The formula (I) 2-(2-imidazolin-2-yl) pyridines and 2-(2-imidazolin-2-yl)quinolines are exceedingly effective herbicidal agents useful for the control of an exceptionally wide variety of herbaceous and woody annual and perennial monocotyledonous and dicotyledonous plants as disclosed in European Patent 41623.

What I claim is:

1. The compound 2-amino-2,3-dimethylbutyramide 2-[(1-carbamoyl-1,2-dimethylpropyl)carbamoyl]-6-(difluoromethoxy)-3-quinolinecarboxylate.

2. The compound 2-[(1-carbamoyl-1,2-dimethylpropyl)carbamoyl]-5-chloro-6-fluoro-3-quinolinecarboxylic acid.

3. The compound 2-[(1-carbamoyl-1,2-dimethylpropyl)carbamoyl]-7-fluoro-3-quinolinecarboxylic acid.

4. The compound 2-[(1-carbamoyl-1,2-dimethylpropyl)carbamoyl]-8-chloro-5-methoxy-3-quinoline carboxylic acid.

* * * * *